United States Patent [19]

Sternberg et al.

[11] Patent Number: 5,552,554
[45] Date of Patent: Sep. 3, 1996

[54] IMIDAZOLE AND TRIAZOLE CARBOXYLATES, AND PROCESSES FOR PREPARING 2,4-OXAZOLIDINEDIONES

[75] Inventors: Jeffrey A. Sternberg, Wilmington; King-Mo Sun, Hockessin, both of Del.; Masuo Toji, Sewell, N.J.; Vincent Witterholt, Wilmington, Del.

[73] Assignee: E. I. Du Pont de Nemours and Company, Wilmington, Del.

[21] Appl. No.: 424,467

[22] PCT Filed: Nov. 5, 1993

[86] PCT No.: PCT/US93/10435

§ 371 Date: May 9, 1995

§ 102(e) Date: May 9, 1995

[87] PCT Pub. No.: WO94/11359

PCT Pub. Date: May 26, 1994

Related U.S. Application Data

[63] Continuation-in-part of Ser. No. 23,239, Feb. 25, 1993, abandoned, which is a continuation-in-part of Ser. No. 988,574, Dec. 10, 1992, abandoned, which is a continuation-in-part of Ser. No. 976,130, Nov. 13, 1992, abandoned.

[51] Int. Cl.⁶ .......... C07D 263/44; C07D 233/60; C07D 249/08
[52] U.S. Cl. .......... 548/226; 548/266.8; 548/334.1
[58] Field of Search .......... 548/266.8, 226, 548/334.1

[56] References Cited

U.S. PATENT DOCUMENTS

| | | | |
|---|---|---|---|
| H1401 | 1/1995 | Campbell | 548/226 |
| 3,954,992 | 5/1976 | Davidson | 424/287 |
| 4,507,310 | 3/1985 | Devoise-Lambert et al. | 514/376 |
| 4,957,933 | 9/1990 | Geffken et al. | 514/376 |
| 5,356,908 | 10/1994 | Geffken et al. | 514/333 |

FOREIGN PATENT DOCUMENTS

| | | | |
|---|---|---|---|
| 0393911 | 10/1990 | European Pat. Off. | C07D 263/44 |
| WO90/12791 | 11/1990 | WIPO | C07D 263/44 |
| 18016 | 9/1993 | WIPO | |
| WO93/22299 | 11/1993 | WIPO | C07D 263/44 |

OTHER PUBLICATIONS

Geffken, D., *Synthesis*, pp. 38–40 (1981).
Abstract 100:6469q re Geffken, D., *Z. Naturforsch.* 38B(8), 1008–1014 (1983).
Abstract 97:182374h re Geffken, D., *Arch. Pharm. (Weinheim, Ger.)*, 315(9), 802–810 (1982).

*Primary Examiner*—D. R. Wilson

[57] ABSTRACT

Processes are described for preparing 2,4-oxazolidinediones having Formula (I)

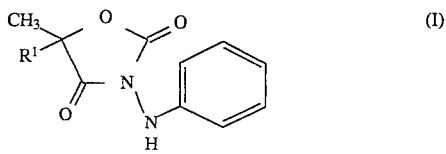

wherein: $R^1$ is phenyl optionally substituted with 1–2 halogens; or 4-phenoxy, 4-(1-phenethyloxy) or 4-benzyloxy each optionally substituted with $R^2$ on the phenyl ring; and $R^2$ is halogen; methyl; or ethyl. 2-Hydroxycarboxylic acid esters are reacted with a carbonylating agent in the presence of a base to give intermediate triazole or imidazole carboxylates. The carboxylates react with phenyl hydrazine in the presence of an acid to give the compounds of Formula (I).

10 Claims, No Drawings

IMIDAZOLE AND TRIAZOLE CARBOXYLATES, AND PROCESSES FOR PREPARING 2,4-OXAZOLIDINEDIONES

This application is a continuation-in-part of application Ser. No. 08/023,239 filed Feb. 25, 1993, now abandoned, which is a continuation-in-part of application Ser. No. 07/988,574 filed Dec. 10, 1992, now abandoned, which is a continuation-in-part of application Ser. No. 07/976,130 filed Nov. 13, 1992, now abandoned.

BACKGROUND OF THE INVENTION

This invention pertains to a process for the preparation of one class of fungicidal oxazolidinone, the 2,4-oxazolidinediones, and intermediate triazole or imidazole carboxylates.

Fungicides that effectively control plant diseases are in constant demand by growers. Plant diseases are highly destructive, difficult to control and quickly develop resistance to commercial fungicides. U.S. Pat. No. 4,957,933 and *Synthesis* 1981, 38–40 disclose the preparation of 2,4-oxazolidinedione fungicides by treatment of N-hydroxy-2-hydroxyhydroxamic acids with 1,1'-carbonyldiimidazole to form dioxazinediones, and subsequent treatment of the dioxazinediones with phenylhydrazine. WO 90/12791 discloses the preparation of 2,4-oxazolidinediones from 2-thioxooxazolidin-4-ones by desulfurization. However, there is a need for a more efficient process. The present invention provides a new efficient process for the preparation of 2,4-oxazolidinediones.

SUMMARY OF THE INVENTION

This invention comprises a process for the preparation of 2,4-oxazolidinediones of Formula I

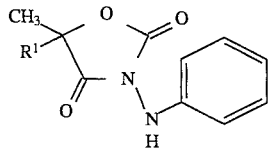

wherein:

$R^1$ is phenyl substituted with 1–2 halogen: or 4-phenoxy, 4-(1-phenethyloxy) or 4-benzyloxy each optionally substituted with $R^2$ on the phenyl ring (i.e., $R^1$ is phenyl substituted with 1.2 halogen, 4-phenoxy, 4-(1-phenethyloxy) or 4-benzyloxy with each 4-phenoxy, 4-(1-phenethyloxy) or 4-benzyloxy optionally substituted with $R^2$ on the phenyl ring): and $R^2$ is halogen: methyl: or ethyl;
comprising 1) reacting a 2-hydroxycarboxylic acid ester of Formula II

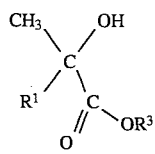

wherein
$R^1$ and $R^2$ are as defined above in Formula I; and
$R^3$ is $C_1$–$C_4$ alkyl;

with a carbonylating agent of Formula III

wherein:

Y is 1-imidazolyl or 1,2,4-triazolyl; provided that Y is 1,2,4-triazolyl when $R^1$ in Formula II is phenyl substituted with 4-(1-phenethyloxy) or 4-benzyloxy (with each 4-(1-phenethyloxy) or 4-benzyloxy optionally substituted with $R^2$ on the phenyl ring as noted above);
and a base to yield an intermediate compound of Formula IV

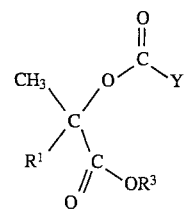

wherein $R^1$, $R^2$, $R^3$ and Y are as defined above:
and 2) subsequently reacting the intermediate of Formula IV as defined above with phenylhydrazine in the presence of an acid to yield a compound of Formula I.

Scheme 1 depicts the process of the present invention.

Scheme 1

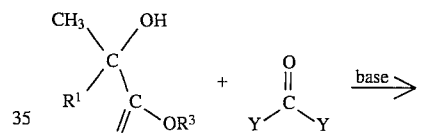

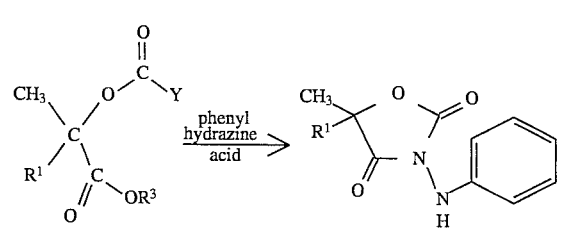

This invention further comprises a compound of Formula IV:

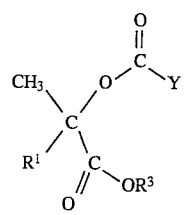

wherein $R^1$ is phenyl substituted with 1–2 halogen, 4-phenoxy, 4-(1-phenethyloxy) or 4-benzyloxy with each 4-phenoxy, 4-(1-phenethyloxy) or 4-benzyloxy optionally substituted with $R^2$ on the phenyl ring;
$R^2$ is halogen, methyl, or ethyl;
$R^3$ is $C_1$–$C_4$ alkyl; and Y is 1-imidazolyl or 1,2,4-triazolyl provided that Y is 1,2,4-triazolyl when $R^1$ is phenyl substituted with 4-(1-phenethyloxy) or 4-benzyloxy (with each 4-(1-phenethyloxy) or 4-benzyloxy optionally substituted with $R^2$ on the phenyl ring as noted above).

DETAILED DESCRIPTION OF THE INVENTION

Preferred processes of the present invention for the preparation of 2,4-oxazolidinediones are processes A to H as follows:

Preferred Process A is the process defined above in Scheme 1 wherein $R^1$ of Formula II is 4-phenoxyphenyl and Y of Formula III is 1-imidazolyl. Preferred Process B is the process defined above in Scheme 1 wherein Y of Formula III is 1,2,4-triazolyl. Preferred Process C is the process of Preferred Process B wherein $R^1$ of Formula II is 4-phenoxyphenyl. Preferred Process D is the process of Preferred Process B wherein $R^1$ is 2,4-difluorophenyl. Preferred Process E is the process defined above in Scheme 1 wherein the compound of Formula III is prepared in situ in the presence of the ester of Formula II. Preferred Process F is the process of Preferred Process E wherein the compound of Formula III is prepared from the alkali metal salt of triazole and phosgene. Preferred Process G is the process defined above in Scheme 1 wherein compounds of Formula IV are not isolated but treated in situ with phenylhydrazine and acid. Preferred Process H is the process of Preferred Process G wherein the compound of Formula IV is prepared using a picoline or mixture of picolines as the organic base, and further comprising filtering the crude reaction mixture containing the compound of Formula IV resulting from step 1) prior to reacting the filtrate with phenylhydrazine in the presence of acetic acid in step 2).

Preferred compounds of Formula IV of the present invention are those as defined above wherein $R^1$ is 4-phenoxyphenyl, and Y is 1,2,4-triazolyl.

Preferred products of Formula I are those wherein $R^1$ is 4-phenoxyphenyl.

The compounds of Formulae I and IV can exist as enantiomers. One skilled in the art will appreciate how to separate said enantiomers. Accordingly, the present invention comprises processes for preparing, the racemic mixtures, the individual enantiomers or optically active mixtures of compounds of Formulae I or IV, or agriculturally suitable salts thereof.

In the above recitations, the term "$C_1$–$C_2$ alkyl" denotes methyl or ethyl. The term "halogen" denotes fluorine, chlorine, bromine or iodine. The term "phenoxy" denotes $OC_6H_5$, "1-phenethyloxy" denotes $OCH(CH_3)C_6H_5$, and "benzyloxy" denotes $OCH_2C_6H_5$.

The present invention comprises a process for the preparation of 2,4-oxazolidinediones as outlined in Scheme 1.

Scheme 1

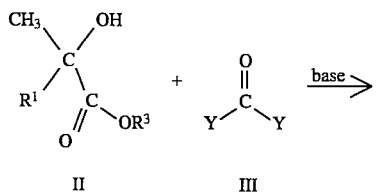

II    III

-continued
Scheme 1

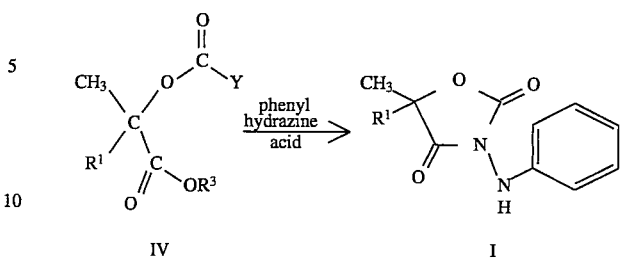

IV    I

Reaction conditions suitable for use in the process of the present invention are as follows. For the conversion of esters of Formula II to compounds of Formula IV, the suitable solvents include inert organic solvents. Preferred solvents are methylene chloride, chloroform, carbon tetrachloride, hexanes, tetrahydrofuran, tert-butyl methyl ether, dioxanes, chlorobenzene, o-dichlorobenzene (ODCB), toluene, xylenes, and suitable combinations thereof. The most preferred solvents are selected from the group consisting of chlorobenzene, ODCB, toluene, and xylenes. Preferred reactants of Formula II are those wherein $R^1$ is 4-phenoxyphenyl, or 2,4-difluorophenyl. Preferred reactants of Formula III are those wherein Y is 1-imidazolyl or 1,2,4-triazolyl. The reaction temperatures can range from about 10° C. to about 75° C. Preferred temperatures are from about 40° C. to about 60° C. Suitable reaction pressures are from about $1.0 \times 10^5$ to about $5.1 \times 10^5$ Pascals. The preferred pressure is $1 \times 10^5$ Pascals. The reaction times are typically 1 to 24 hours, preferably 3 to 6 hours. A suitable ratio of Formula III to II is from about 1:1 to 2:1. The preferred ratio is from about 1.1:1 to 1.8:1. Suitable bases for this reaction include trialkylamine, imidazole, pyridine, picoline or other substituted pyridine, or mixtures thereof.

For the conversion of compounds of Formula IV to 2,4-oxazolidinediones of Formula I, suitable solvents are as noted above for the condensation of Formulae II and III. The preferred solvents are those disclosed above as preferred. The reaction temperatures are from about 0° C. to about 75° C. Preferred temperatures are from about 10° C. to about 50° C. Reaction pressures are from about $1.0 \times 10^5$ to about $5.1 \times 10^5$ Pascals. The preferred pressure is $1 \times 10^5$ Pascals. The reaction times are typically 1 to 24 hours, preferably 2 to 6 hours. The acids suitable for catalyzing the reaction are selected from the group consisting of alkyl and aryl carboxylic acids, trialkylammonium halides and combinations thereof. The preferred acids are acetic acid and triethylammonium chloride. The most preferred acid is acetic acid. Suitable ratios of phenylhydrazine to Formula IV is from about 2:1 to 1:1. The preferred ratio is from about 1.6:1 to 1.1:1.

The carbonylating agent of Formula III may be added as a pure compound, a solution of the pure compound in an inert solvent, or prepared in situ in the presence of the ester of Formula II. The preferred process involves preparation of the carbonylating agent in situ.

Methods for preparing compounds of Formula III, including in situ methods, from phosgene [or phosgene equivalents such as diphosgene (trichloromethyl chloroformate) or triphosgene (bis(trichloromethyl)carbonate)] and either imidazole or triazole are known in the art (see *Org. Syntheses*. Coll. Vol. 5, 201, (1973)). Reactions wherein HCl is liberated require a base to trap the acid. A suitable base is a trialkylamine or a picoline, or combinations thereof. The preferred base is a picoline. 1,1'-Carbonylditriazole (Formula III wherein Y=1,2,4-triazolyl) can also be prepared by treating a metal alkali salt of triazole, preferably the potassium salt, with phosgene (or phosgene equivalent) in a solvent. No additional base is required when the metal salt of the triazole is used. Phase transfer catalysts may be added to reactions wherein the triazole salt has low solubility in the solvent. Any phase transfer catalyst known to one skilled in the art is suitable. The triazole salt is prepared by treating triazole with a suitable base, such as sodium hydroxide or sodium ethoxide. The preferred relative amount of alkali metal base to triazole to phosgene is 1.0:1.4:0.6.

Base is also necessary to catalyze the condensation of Formulae II and III to yield IV. As previously stated, suitable base catalysts are trialkylamines, imidazole, pyridine, picolines or other substituted pyridines. When 1,1'-carbonyldiimidazole is used (Formula III wherein Y=1-imidazolyl), the imidazole which is liberated upon reaction with Formula II serves as the catalyst. When 1,1'-carbonylditriazole is used, the preferred base is pyridine, a picoline, or a mixture of picoline isomers.

Compounds of Formula IV may be isolated, such as by filtration or other suitable means, and purified, or treated in situ with phenylhydrazine and acid to form the 2,4-oxazolidinediones of Formula I. Suitable acids include alkyl and aryl carboxylic acids, trialkylammonium halides and combinations thereof. Preferred is acetic acid. The preferred method involves treatment of Formula IV in situ with phenylhydrazine. After the formation of the carbamate of Formula IV is complete, excess carbonylating agent can be decomposed by the addition of water.

The 2-hydroxycarboxylic acid esters of Formula II can be prepared by a number of methods known in the literature.

(1) They can be formed from the corresponding 2-hydroxycarboxylic acids by esterification as is well known in the literature. The 2-hydroxycarboxylic acids can be prepared from methyl ketones by formation of cyanohydrins, then hydrolysis, as is also known. For example, *Org. Syntheses*. Coll. Vol. 4, 58 (1968) teaches the preparation of atrolactic acid from acetophenone.

(2) The esters of Formula II can also be synthesized from ketone cyanohydrins by treatment with alcohols in the presence of HCl to afford the iminoether hydrochlorides, followed by hydrolysis.

(3) A third method known for preparing 2-hydroxycarboxylic acids and esters involves treating 2-keto-acids or 2-keto-esters with nucleophilic-organometallic reagents such as Grignard reagents, and alkyl- and aryl-lithium reagents. For example, R. G. Salomon et al. teaches the preparation of some esters of Formula II by the addition of aryl-Grignard reagents to pyruvate esters (*J. Org. Chem.* (1982), 47, 4692). Similarly, some 2-hydroxycarboxylic acids may be prepared by the regioselective nucleophilic addition of an aryl organometallic reagent to the metal salt (e.g., sodium salt) of pyruvic acid.

(4) Another method described in the literature for preparing some 2-aryl-2-hydroxyesters and acids is by acylation of aromatic rings with activated carbonyl compounds in the presence of a protic or Lewis acid. Aromatic substrates capable of undergoing reactions of this type are benzene, diphenyl ether, and other aromatic compounds known to be of sufficient reactivity to undergo Friedel-Crafts-type reactions.

In the case of mono-substituted benzene derivatives, the acylation occurs preferentially, but not necessarily exclusively, para to the point of attachment of the substituent. For example, see *Org. Syntheses*. Coll. Vol. 3, 326, (1955), Salomon et al., *J. Org. Chem.*, (1982), 47, 4692. and U.S. Pat. No. 4,922,010. Carbonyl compounds known to undergo this acylation reaction include pyruvate esters and acids, glyoxylate esters and acids, and diesters of oxomalonates. The acids used in the acylation reaction can either be protic in nature, for example, a mixture of acetic and sulfuric acid, or a Lewis acid such as aluminum chloride, tin tetrachloride, titanium tetrachloride, or other Lewis acid known to effect Friedel-Crafts-type reactions. The acid can be used either catalytically or in excess. In some cases, the acid may react destructively with the carbonyl substrate and excess carbonyl compound must be used.

The present invention further comprises compounds of Formula IV

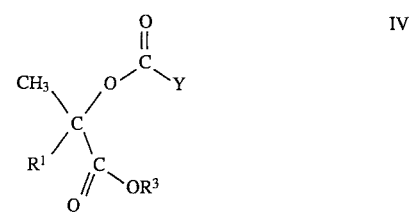

wherein $R^1$ is phenyl substituted with 1-2 halogen, 4-phenoxy, 4-(1-phenethyloxy) or 4-benzyloxy with each 4-phenoxy, 4-(1-phenethyloxy) or 4-benzyloxy optionally substituted with $R^2$ on the phenyl ring;

$R^2$ is halogen, methyl, or ethyl:

$R^3$ is $C_1$–$C_4$ alkyl; and

Y is 1-imidazolyl or 1,2,4-triazolyl provided that Y is 1,2,4-triazolyl when $R^1$ is phenyl substituted with 4-(1-phenethyloxy) or 4-benzyloxy with each 4-(1-phenethyloxy) or 4-benzyloxy optionally substituted with $R^2$ on the phenyl ring.

These compounds are prepared as described above by the process of the present invention. Compounds of Formula IV can be isolated by treating the reaction mixture of Formula II, Formula III and base with water or ice, and extracting with a water-immiscible organic solvent. The organic solvents are then combined, dried, and evaporated. Further purification can be accomplished by chromatography or recrystallization. Compounds of Formula IV are useful as intermediates in the preparation of compounds of Formula I as previously defined using the reaction as defined above in Scheme 1.

The following Examples demonstrate the process and compounds of the present invention.

EXAMPLE 1

Preparation of 5-Methyl-5-(4-phenoxyphenyl)-3-phenylamino-2,4-oxazolidinedione Using Pre-Formed 1,1'-Carbonyldiimidazole A mixture of 14.3 g of ethyl 2-(4-phenoxyphenyl)lactate (34 g of a mixture containing 14.3 g of ethyl 2-(4-phenoxyphenyl)lactate and 19.7 g of diphenyl ether), 9.7 g of 1,1'-carbonyldiimidazole and 100 mL of methylene chloride was agitated at 25° C. for 19 h. Water (0.30 mL) was added and the mixture was agitated for 15 min. Then, 5 mL of acetic acid and 7.4 g of phenylhydrazine were added. After agitating at 25° C. for 24 h, 100 mL of water was added. The pH was lowered to 2 with hydrochloric acid, and the aqueous layer was removed. After washing the methylene chloride layer with 50 mL of water, the solvent was evaporated under vacuum. The oily residue was mixed with 150 mL hexane and 15 mL of ethyl acetate, heated to 65° C., cooled to 20° C., and then filtered. The solids were washed with 100 mL of a mixture of 20 mL ethyl acetate and 80 mL of hexane and then dried. The title product (15.2 g) was obtained with a m.p. of 137°–139° C.

EXAMPLE 2

Preparation of 5-Methyl-5-(4-phenoxyphenyl)-3-phenylamino-2,4-oxazolidinedione With 1,1'-Carbonyldiimidazole Prepared In Situ A mixture of 28.6 g of ethyl 2-(4-phenoxyphenyl)lactate (70.8 g of a mixture containing 28.6 g of ethyl 2-(4-phenoxyphenyl)lactate and 42.2 g of diphenyl ether), 100 mL of chlorobenzene, 47 g of N,N-dimethylbenzylamine, and 17 g of imidazole was heated to 60° C. Phosgene (16 g) was added subsurface over 2 h. After holding for 2 h at 60° C., the reaction was cooled to 20° C. Water (0.2 g) was added, and the mixture was agitated for 15 min. Then, 16 g of phenylhydrazine was added and the mixture was agitated for 16 h at 25° C. Water (100 mL) was added, and then hydrochloric acid added to adjust the pH to 1–2. The aqueous layer was separated and washed with 25 mL of chlorobenzene. The combined organic layers were washed once with 50 mL of water. Hexane (100 mL) was added, and then the mixture was heated to 50° C. Another 100 mL of hexane was added, and the mixture was held at 50° C. for another 1 h. The reaction was then cooled to 15° C. and filtered. The solids were washed with 200 mL of a mixture of 40 mL of 2-propanol and 160 mL of hexane. After drying, 26 g of the title compound with a m.p. of 140°–142° C. was obtained.

EXAMPLE 3

The process of Example 2 was repeated using 150 mL of tert-butyl methyl ether in place of 100 mL of chlorobenzene. 24.1 g of 5-methyl-5-(4-phenoxyphenyl)-3-phenylamino-2,4-oxazolidinedione was obtained, m.p. 140°–141 ° C.

EXAMPLE 4

Preparation of 5-Methyl-5-(2,4-difluorophenyl)-3-phenylamino-2,4-oxazolidinedione Using Pre-Formed 1,1'-Carbonyldiimidazole 1.3 Grams of methyl 2-(2,4-difluorphenyl)lactate ($[\alpha]_D^{25}$=+12.7±1°, c=0.79 g/100 mL in chloroform), 1.10 g of 1,1'-carbonyldiimidazole, and 25 mL of methylene chloride was agitated at 25° C. for 18 h. Acetic acid (1.0 mL) and 0.81 g of phenylhydrazine were added and the mixture was agitated for 16 h at 25° C. Water (25 mL) was added, and the organic layer was separated. The aqueous layer was extracted with 50 mL of methylene chloride. The combined organic layers were washed with 50 mL of H$_2$O, and then the organic solvent was evaporated. The residue was recrystallized from 2 mL of ethyl acetate and 10 mL of hexane to yield 1.1 g of the title compounds, m.p. 89°–108° C. High Pressure Liquid Chromatography (HPLC) analysis showed the product consisted of 56% S-enantiomer and 28% R-enantiomer. The optical rotation of the title compound was $[\alpha]_D^{25}$ =–11.0±0.8°, c=1.02 g/100 mL in chloroform.

EXAMPLE 5

Preparation of 5-Methyl-5-(4-phenoxyphenyl)-3-phenylamino-2,4-oxazolidinedione With 1,1'-Carbonyldi(1,2,4-triazole) Prepared In Situ A mixture of 28.6 g of ethyl 2-(4-phenoxyphenyl)lactate (35.3 g of a mixture containing 28.6 g of ethyl 2-(4-phenoxyphenyl)lactate and 6.7 g of diphenyl ether), 12.4 g 1,2,4-triazole, 32 g of triethylamine, and 150 mL of xylene was heated to 110° C. until all solids dissolved. The solution was then cooled to 50° C. Phosgene (12.4 g) was added subsurface over 2 h, and then the mixture was held at 50° C. for an additional 3 h. The reaction mass was then cooled to 25° C. Water (0.2 g) was added, and the mixture was agitated for 15 min. Then 17 g of phenylhydrazine was added. After agitation at 25° C. for 4 h, 60 mL of hot water was added. Hydrochloric acid was added to lower the pH to 3. The organic layer was separated and washed with 50 mL of hot water. The xylene solvent was partially distilled at 1.3×10$^4$ Pa (115 mL distillate was removed). The solution was held at 60° C. until the product fully precipitated. Then, a mixture of 200 mL of hexane and 20 mL of 2-propanol was added over 30 min. After holding the mixture at 65° C. for another 1 h, the slurry was cooled to 20° C. and then filtered. The solid was washed with 200 mL of a mixture of 180 mL of hexane and 20 mL of 2-propanol. The solids were dried to yield 28.6 g of the title compound, m.p. 140°–141° C.

EXAMPLE 6

The process of Example 5 was repeated using 12.4 g of diphosgene (trichloromethyl chloroformate) in place of phosgene and using toluene in place of xylene. 24.1 g of 5-methyl-5-(4-phenoxyphenyl)-3-phenylamino-2,4-oxazolidinedione, m.p. 139°–141° C., was obtained.

EXAMPLE 7

Preparation of 5-Methyl-5-(4-phenoxyphenyl)-3-phenylamino-2,4-oxazolidinedione Using the Potassium salt of 1,2,4-Triazole A mixture of 20.7 g of 1,2,4-triazole, 19.8 g of 85% potassium hydroxide pellets, and 150 mL of xylene was heated to reflux under high turbulence using a Dean-Stark water trap. The mixture was refluxed until the water was completely removed. The slurry was then cooled to 50° C., and 28.6 g of ethyl 2-(4-phenoxyphenyl)lactate (33.2 g of a mixture containing 28.6 g of ethyl 2-(4-phenoxyphenyl)lactate and 4.6 g of diphenyl ether), 36 mL of 4-picoline, and 5 g of tricaprylylmethylammonium chloride were added. Phosgene (14 g) was added subsurface over a 2 h period at 50° C. The reaction mixture was held at 50° C. for another 4 h. After cooling to 25° C., 0.3 g of water was added, the mixture was stirred for 15 min., and then 17 g of phenylhydrazine and 5 mL of acetic acid were added. After agitating for 4 h at 25°–30° C., 100 mL of hot water was added, followed by hydrochloric acid to lower the pH to 2. The aqueous layer was removed, and the organic layer was washed with 50 mL of hot water. The organic layer was distilled under vacuum (2.0×10$^4$ Pa) until 65 mL of xylene was removed. After cooling to 60° C., the product was allowed to crystallize. A mixture of 200 mL of hexane and 20 mL of 2-propanol was added to 65° C. over 1 h. After holding the reaction mixture at 65° C. for another 1 h, and then cooling to 20° C. the solids were isolated by filtration. The solids were washed with a mixture of 200 mL of hexane and 20 mL of 2-propanol. The solid was dried yielding 29.1 g of the title compound.

EXAMPLE 8

Preparation of 5-Methyl-5-(4-phenoxyphenyl)-3-phenylamino-2,4-oxazolidinedione Using the Sodium salt of 1,2,4-Triazole Prepared In Situ A mixture of 20.7 g of 1,2,4-triazole, 200 mL of toluene, and 58.3 g of 25% sodium methoxide in methanol was distilled under high turbulence until the temperature reached 110° C. and 120 mL of distillate was collected. The slurry was then cooled to 50° C. Then, 28.6 g of ethyl 2-(4-phenoxyphenyl)lactate (33.2 g of a mixture containing 28.6 g of ethyl 2-(4-phenoxyphenyl)lactate and 4.6 g of diphenyl ether), 36 mL of 2-picoline, and 5 g of tricaprylylmethylammonium chloride were added. Phosgene (14 g) was added subsurface at 50° C. over a 2 h period, and then the reaction was held at 50° C. for another 4 h. After cooling to 25° C., 0.30 g of water was added, the mixture was agitated for 15 min., and then 17 g of phenylhydrazine and 5 mL of acetic acid were added. After agitating at 25°–30° C. for 4 h, 100 mL of hot water and 35 mL of concentrated hydrochloric acid were added. The aqueous layer was separated and the organic layer was washed with 50 mL of hot water. The organic layer was distilled under vacuum ($2.6 \times 10^4$ Pa) until 65 mL of toluene was collected. The product was allowed to crystallize at 60° C. and then a mixture of 200 mL of hexane and 20 mL of 2-propanol was added at 65° C. over 1 h. After holding at 65° C. for another 1 h followed by cooling to 20° C., the product was filtered off and washed with 200 mL of 10:1 hexane:2-propanol. The product was dried to yield 24 g of the title compound, m.p. 140°–141° C.

EXAMPLE 9

Preparation of 5-Methyl-5-(4-phenoxyphenyl)-3-phenylamino-2,4-oxazolidinedione Using the Pre-Formed Sodium salt of 1,2,4-Triazole A mixture of 15.2 g of 1,2,4-triazole, sodium salt (90% purity), 75 mL of toluene, 14.3 g of ethyl 2-(4-phenoxyphenyl)lactate (16.6 g of a mixture containing 14.3 g of ethyl 2-(4-phenoxyphenyl)lactate and 2.3 g of diphenyl ether), 2.5 g of tricaprylylmethylammonium chloride, and 18 mL of 4-picoline was heated to 50° C. Phosgene (7.0 g) was added at 50° C. over 2 h. After holding the reaction mixture at 50° C. for 4 h, the reaction mass was cooled to 20° C. Water (0.15 g) was added, the mixture was agitated for 15 min., and then 2 mL of acetic acid and 8.5 g of phenylhydrazine were added. After agitating at 25° C. for 15 h, 50 mL of hot water, and 18 mL of concentrated, hydrochloric acid were added. The layers were separated and the organic layer was washed with 25 mL of hot water. The organic layer was distilled under vacuum ($2.0 \times 10^4$ Pa) until 31 mL of distillate was removed. The product was crystallized at 50° C., and then 90 mL of hexane and 10 mL of 2-propanol were added at 60° C. After cooling to 20° C., the solids were collected on a filter and washed with 10:1 hexane:2-propanol. The product was dried to yield 9.7 g of the title compound.

EXAMPLE 10

Preparation of 2-Ethoxy-1-methyl-2-oxo-1-(4-phenoxy-phenyl)ethyl 1H-1,2,4-triazole-1-carboxylate A mixture of 6.9 g of 1,2,4-triazole, 100 mL of toluene, 14.3 g of ethyl 2-(4phenoxyphenyl)lactate, and 20 g of triethylamine was heated to 103° C. to dissolve the triazole and then cooled to −60° C. Phosgene (6.4 g) was added at 57°–60° C. over 2.5 h. After holding the reaction mixture at 59°–60° C. for 1.25 h, the reaction mixture was cooled to −5° C. Ice (100 g) was added, and the temperature dropped to −8° C. The aqueous layer was separated and extracted one time with 15 mL of toluene. The organic layers were combined and washed with cold water (2 times with 25 mL), dried (MgSO$_4$), filtered, and evaporated in vacuo to yield 19.6 g of the title compound as a viscous oil. $^1$H NMR (300 MHz, CDCl$_3$): δ8.85 (s, 1H), 8.08 (s,1H), 7.59–7.00 (m, 11H), 4.25 (m,2H), 2.18 (s,3H), 1.23 (t,3H).

EXAMPLE 11

Preparation of 5-Methyl-5-(4-phenoxyphenyl)-3-phenylamino-2,4-oxazolidinedione using a mixture of picoline isomers as the base Phosgene (13 g) was added subsurface to a mixture of 100 mL xylene, 40 mL of mixed picoline isomers, 28.6 g of 2-(4-phenoxyphenyl)lactate, 5.4 g of diphenyl ether, and 13.8 g of 1,2,4-triazole at 50° C. over 2 h. After agitating at 50° C. for 3 h, the reaction mass was cooled to 25° C. and then filtered. The solids were washed with two 25 mL portions of xylene. To the combined filtrates, 5 drops of water were added, agitated for 15 minutes, and then 5 mL of acetic acid and 17 g of of phenylhydrazine were added. The reaction mass was heated to 50° C. and agitated for 3 h. After adding 80 mL of water and concentrated aqueous HCl until the pH was 1.5, the layers were separated. The xylene layer was washed with 50 mL of water acidified to pH 1.5, and the layers were separated. The xylene layer was washed with 50 mL of water and then distilled under vacuum to remove 50 mL of distillate. After crystallizing at 60° C., a mixture of 200 mL hexane and 20 mL of 2-propanol was added at 60°–65° C. After cooling to 20° C., the solids were collected on a filter and washed with 10:1 hexanes:2-propanol. The solids were dried to yield the title compound in high yield.

EXAMPLE 12

Preparation of 5-Methyl-5-(4-phenoxyphenyl-3-phenylamino--2,4-oxazolidinedione using sodium triazolide prepared in situ A solution of 12.4 g 1,2,4-triazole dissolved in 34.6 g of 25% sodium methoxide in methanol was added dropwise to 150 mL of xylene at 100°–110° C. while distilling off the methanol as the addition occurred. After all of the methanol solution was added, the temperature was raised to 140° C. while removing additional distillate. After cooling to 50° C. 30 mL of mixed picolines, 2.0 g of 1,2,4-triazole, 28.6 g of 2-(4phenoxyphenyl)lactate, and 11.1 g of diphenyl ether were added. Phosgene, 12.5 g, was added subsurface at 50° C. over 3 h. After holding the reaction mixture at 50° C. for another 3 h, 5 drops of water were added, and then 8 g of sodium acetate and 17 g of phenylhydrazine were added. After holding at 50° C. for another 3 h, 80 mL of water, 100 mL of xylene, and concentrated aqueous HCl to pH 1.5 were added sequentially. The layers were separated and 50 mL of water was added to the xylene layer. After adding concentrated aqueous HCl to pH 1.5, the layers were separated. The organic layer was washed with water, and then vacuum distilled until 100 mL of xylene was removed. After crystallizing at 60° C., 200 mL of hexane and 20 mL of 2-propanol were added. After cooling to 20° C., the solids were collected on a filter and washed with 10:1 hexane:2- propanol. The solids were dried to yield the little compound in high yield.

What is claimed is:

1. A process for the preparation of 2.4-oxazolidinediones of Formula I

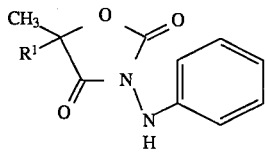

wherein:

R¹ is phenyl substituted with 1–2 halogen or R¹ is phenyl substituted with 4-phenoxy, 4-(1-phenethyloxy) or 4-benzyloxy with each 4-phenoxy, 4-(1-phenethyloxy) or 4-benzyloxy optionally substituted with R² on the phenyl ring; and R² is halogen; methyl; or ethyl;

comprising 1) reacting a 2-hydroxycarboxylic acid ester of Formula II

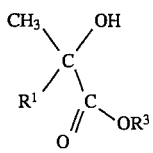

wherein

R¹ and R² are defined as above for Formula I; and

R³ is $C_1$–$C_4$ alkyl;

with a base and a carbonylating agent of Formula III

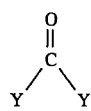

wherein

Y is 1-imidazole or 1,2,4-triazolyl, provided that Y is 1,2,4-triazolyl when R¹ in Formula II is phenyl substituted with 4-(1-phenethyloxy) or 4-benzyloxy with each 4-(1-phenethyloxy) or 4-benzyloxy optionally substituted with R² on the phenyl ring; to yield an intermediate compound of Formula IV:

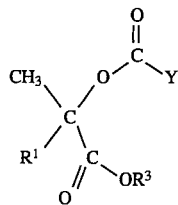

wherein

R¹, R², R³ and Y are defined as above: and 2) reacting a compound of Formula IV as defined above with phenylhydrazine in the presence of an acid to yield a compound of Formula I.

2. A process according to claim 1 wherein R¹ of Formula II is 4-phenoxyphenyl or 2,4-difluorophenyl.

3. A process according to claim 1 wherein R¹ of product Formula I is 4-phenoxyphenyl.

4. A process according to claim 1 further comprising preparing in situ the carbonylating agent of Formula III by reacting 1) phosgene, 2) one of imidazole or 1,2,4-triazole and 3) an organic base selected from the group consisting of trialkylamine, pyridine, picoline or other substituted pyridine, or by reacting 1) phosgene and 2) an alkali metal salt of 1,2,4-triazole.

5. A process according to claim 4 wherein the carbonylating agent of Formula III is prepared in situ by the reaction of phosgene and an alkali metal salt of 1,2,4-triazole.

6. A process according to claim 1 wherein the compound of Formula IV is prepared using at least one picoline as the organic base.

7. A process according the claim 6 wherein the reaction mixture of step 1) is filtered prior to step 2).

8. A process according to claim 7 wherein the acid employed in step 2) is acetic acid.

9. A compound of Formula IV

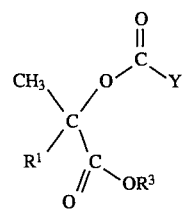

wherein

R¹ is phenyl substituted with 1–2 halogen; or 4-phenoxy, R¹ is phenyl substituted with 4-(1-phenethyloxy) or 4-benzyloxy each optionally substituted with R² on the phenyl ring;

R² is halogen, methyl or ethyl:

R³ is $C_1$–$C_4$ alkyl; and

Y is 1-imidazolyl or 1,2,4-triazolyl provided that Y is 1,2,4-triazolyl when R¹ is phenyl substituted with 4-(1-phenethyloxy) or 4-benzyloxy with each 4-(1-phenethyloxy) or 4-benzyloxy optionally substituted with R² on the phenyl ring.

10. A compound of claim 9 wherein R¹ is 4-phenoxyphenyl and Y is 1,2,4-triazolyl.

* * * * *